United States Patent
Tanaka et al.

(10) Patent No.: US 9,686,983 B2
(45) Date of Patent: Jun. 27, 2017

(54) TOBACCO AXILLARY BUD GROWTH INHIBITOR AND METHOD FOR INHIBITING TOBACCO AXILLARY BUD GROWTH

(71) Applicant: SDS BIOTECH K. K., Tokyo (JP)

(72) Inventors: Motoki Tanaka, Ibaraki (JP); Keijitsu Tanaka, Ibaraki (JP); Takeshi Shibuya, Ibaraki (JP); Eiji Ikuta, Tokyo (JP); Kotaro Yoshinaga, Tokyo (JP); Yuki Yamaguchi, Ibaraki (JP)

(73) Assignee: SDS BIOTECH K.K., Tokyo (JP)

( * ) Notice: Subject to any disclaimer, the term of this patent is extended or adjusted under 35 U.S.C. 154(b) by 0 days.

(21) Appl. No.: 14/892,901

(22) PCT Filed: May 27, 2013

(86) PCT No.: PCT/JP2013/064631
§ 371 (c)(1),
(2) Date: Nov. 20, 2015

(87) PCT Pub. No.: WO2014/192059
PCT Pub. Date: Dec. 4, 2014

(65) Prior Publication Data
US 2016/0113275 A1   Apr. 28, 2016

(51) Int. Cl.
*A01N 37/10* (2006.01)
*A01N 31/02* (2006.01)

(52) U.S. Cl.
CPC .............. *A01N 37/10* (2013.01); *A01N 31/02* (2013.01)

(58) Field of Classification Search
None
See application file for complete search history.

(56) References Cited

U.S. PATENT DOCUMENTS

| | | | |
|---|---|---|---|
| 3,672,866 A | 6/1972 | Damiano | |
| 4,046,809 A | 9/1977 | Wilcox | |
| 4,123,250 A | 10/1978 | Kupelian | |
| 4,627,869 A | 12/1986 | Chang | |
| 4,685,951 A | 8/1987 | Nishimuta et al. | |
| 8,865,624 B2 * | 10/2014 | Tanaka | A01N 31/02 504/129 |

FOREIGN PATENT DOCUMENTS

| | | |
|---|---|---|
| JP | 61-36203 A | 2/1986 |
| JP | 61-158904 A | 7/1986 |
| JP | 62-298503 A | 12/1987 |
| JP | 62-298504 A | 12/1987 |
| WO | 2012/029446 A1 | 3/2012 |
| WO | 2012/172621 A1 | 12/2012 |

OTHER PUBLICATIONS

International Search Report of PCT/JP2013/064631 dated Jul. 2, 2013.

* cited by examiner

*Primary Examiner* — Mina Haghighatian
*Assistant Examiner* — Luke Karpinski
(74) *Attorney, Agent, or Firm* — Sughrue Mion, PLLC

(57) ABSTRACT

An inhibitor for tobacco axillary bud growth, containing chlorthal-dimethyl and aliphatic alcohol selected from decyl alcohol, 2-ethyl hexanol and geraniol in combination; and a method for inhibiting tobacco axillary bud growth, which includes applying the inhibitor for tobacco axillary bud growth.

4 Claims, No Drawings

TOBACCO AXILLARY BUD GROWTH INHIBITOR AND METHOD FOR INHIBITING TOBACCO AXILLARY BUD GROWTH

CROSS REFERENCE TO RELATED APPLICATIONS

This is a National Stage of International Application No. PCT/JP2013/064631 filed May 27, 2013, the contents of which are incorporated herein by reference in its entirety.

TECHNICAL FIELD

The present invention relates to an inhibitor for tobacco axillary bud growth comprising dimethyl tetrachloroterephthalate (chlorthal-dimethyl) and a specific aliphatic alcohol as an active ingredient; and a method for inhibiting tobacco axillary bud growth by applying the inhibitor for tobacco axillary bud growth.

BACKGROUND ART

A labor for removing axillary buds just before harvesting of tobacco is necessary for securing the yield and quality of leaf tobacco. However, in order to perform the labor by hand work, a huge amount of work is required. Therefore, nowadays, a method involving spraying an inhibitor for tobacco axillary bud growth has been developed and widely used.

As an inhibitor for tobacco axillary bud growth which has been widely used from the Showa 30's (1955-1964), there are known inhibitors including, as an active ingredient, maleic hydrazide or a salt thereof, having penetrating migration characteristics. The inhibitor is actually used at a concentration as high as about 5,000 ppm and is poor in terms of sustained chemical efficacy. Hence, there has been a problem in that a large amount of the inhibitor is required. Further, hydrazine produced by decomposition of maleic hydrazide exhibits oncogenic potential, and hence use of the inhibitor is currently restricted.

Therefore, in recent years, a contact-type inhibitor for tobacco axillary bud growth, which is sprayed by contact with stem, has been used. As the contact-type inhibitor, there are known, for example, an inhibitor including a saturated aliphatic alcohol as an active ingredient and an inhibitor including a dinitroaniline-based chemical substance as an active ingredient.

The inhibitor for axillary bud growth including a saturated aliphatic alcohol as an active ingredient has a high effect of killing axillary buds by contact. However, the inhibitor including a saturated aliphatic alcohol as an active ingredient is poor in terms of sustained chemical efficacy and requires spraying of the inhibitor at least twice in order to prevent elongation of axillary buds in the later growth period. In addition, attachment of the sprayed inhibitor to leaves at the time of use causes bleaching, another harmful effect of the inhibitor, and reduction in quality of the leaves. Further, as the inhibitor is dropped and accumulated at the base part of a plant, all stem bases are necrotized, resulting in killing the plant.

On the other hand, the inhibitor including a dinitroaniline-based chemical substance as an active ingredient is disclosed in, for example, U.S. Pat. No. 3,672,866 A (Patent Document 1), U.S. Pat. No. 4,046,809 A (Patent Document 2) and U.S. Pat. No. 4,123,250 A (Patent Document 3). The inhibitor including a dinitroaniline-based compound as an active ingredient contains a certain organic solvent. The inhibitor has an effect of stopping growth of axillary buds by dehydrating and necrotizing axillary buds by contact of the dinitroaniline-based chemical substance and the organic solvent with the axillary buds and allowing the above-mentioned chemical substance to be absorbed from the axillary bud plumule part or from wounds after removal of the axillary buds to inhibit cell division and has a high effect of inhibiting formation and elongation of axillary buds.

However, the inhibitor including a dinitroaniline-based chemical substance as an active ingredient has the following problems, for example. The inhibitor sometimes causes harmful effects such as deformation of young leaves of the upper node, lack in expansion, necrosis of mesophyll, damages of the petiole parts of middle or upper leaves, developmental disorders of adventitious roots, and necrosis immediately after spraying; and induces diseases such as hollow heart, crown rot, and gray mold from wound sites formed in the petiole base by the harmful effects to cause adverse effects on the yield and quality of leaf tobacco.

An inhibitor comprising a chlorthal-dimethyl-based chemical substance as an active ingredient is disclosed in, for example, U.S. Pat. No. 4,627,869 (JP H05-19521 B; Patent Document 4). Chlorthal-dimethyl has a high effect of inhibiting formation and elongation of axillary buds as with a dinitroaniline-based chemical substance.

Patent Document 4 discloses a method of applying chlorthal-dimethyl to plants followed by an application of fatty alcohols having 6 to 12 carbon atoms, as a known substance which can be used singly as an inhibitor for tobacco axillary bud growth, 5 to 14 days later (sequential application) but it does not indicate experimental data and does not suggest or disclose the improvement in effect of inhibiting the tobacco axillary bud growth of both of the ingredients by the sequential application, either. There has been no document so far, which teaches that the effect of inhibiting the formation and growth of tobacco axillary buds can be synergistically improved through the application of an inhibitor by preparing the formulation by mixing chlorthal-dimethyl and aliphatic alcohol having 6 to 20 carbon atoms, or by preparing the formulation of the both ingredients independently and appropriately mixing the two before the use.

Furthermore, WO 2012/029446 (Patent Document 5) discloses that the effect of inhibiting the tobacco axillary buds can be synergistically improved by combining chlorthal-dimethyl and an ultra-long chain fatty acid synthesis inhibitor.

However, conventional inhibitors for tobacco axillary bud growth including chlorthal-dimethyl as an active ingredient had a high effect of inhibiting the axillary bud but had a low penetration into the plant body, and hence the inhibitor had to be used at a high concentration. Accordingly, it is necessary to use the inhibitor repeatedly until harvest and a large amount of the inhibitor is required. In addition, the inhibitor remains at a high concentration on the surface of the tobacco leaves and hence there has been a problem in that the remaining inhibitor has a harmful effect on the quality of the leaf tobacco.

As mentioned above, the contact inhibitor for axillary bud growth currently used in cultivation of tobacco have many problems yet to be solved from the viewpoint of sustainment of the chemical efficacy and occurrence of harmful effects.

Therefore, a contact inhibitor for tobacco axillary bud growth which is effective in a small amount, is excellent in terms of sustained chemical efficacy, induces no harmful effect, and can contribute to improvement in labor productivity has been desired.

PRIOR ART DOCUMENT

Patent Document

[PATENT DOCUMENT 1] U.S. Pat. No. 3,672,866 A
[PATENT DOCUMENT 2] U.S. Pat. No. 4,046,809 A
[PATENT DOCUMENT 3] U.S. Pat. No. 4,123,250 A
[PATENT DOCUMENT 4] U.S. Pat. No. 4,627,869 A (JP H05-19521 B)
[PATENT DOCUMENT 5] WO 2012/029446

SUMMARY OF INVENTION

Problem to be Solved by the Invention

An object of the present invention is to provide an inhibitor for tobacco axillary bud growth, which shows sustained chemical efficacy in a small amount, induces no harmful effect and no disease, and can contribute to improvement in labor productivity.

Means to Solve the Problem

The inventors of the present invention have made various studies on the inhibitory effect on the tobacco axillary bud growth by combining chlorthal-dimethyl and various compounds, particularly aliphatic alcohol having 6 to 12 carbon atoms, which are known as a compound that can be used singly as an inhibitor of tobacco axillary bud to develop a novel inhibitor for tobacco axillary bud growth. As a result, the inventors have found that the penetration of chlorthal-dimethyl into the tobacco plant body can be improved by combining chlorthal-dimethyl and a specific aliphatic alcohol (decyl alcohol, 2-ethyl hexanol or geraniol), to thereby enable the inhibitor exhibit the effect of inhibiting axillary bud even in a small amount and to improve the effect of inhibiting the formation and elongation of axillary buds synergistically. Thus, the present invention was accomplished.

The present invention relates to the following inhibitor for tobacco axillary bud growth and method for inhibiting tobacco axillary bud growth.
(1) An inhibitor for tobacco axillary bud growth, comprising chlorthal-dimethyl and aliphatic alcohol selected from decyl alcohol, 2-ethyl hexanol and geraniol as an active ingredient.
(2) The inhibitor for tobacco axillary bud growth as described in (1) above, wherein the ratio of chlorthal-dimethyl and aliphatic alcohol by mass is 1:2,500 to 1:50.
(3) The inhibitor for tobacco axillary bud growth as described in (1) or (2) above, which is used by controlling the chlorthal-dimethyl concentration and the aliphatic alcohol concentration in the treatment solution to be applied to tobacco seedlings to 0.001 to 0.01 mass % and 0.5 to 2.5 mass %, respectively.
(4) A method for inhibiting tobacco axillary bud growth, comprising applying the inhibitor for tobacco axillary bud growth described in any one of (1) to (3) above.
(5) The method for inhibiting tobacco axillary bud growth as described in (4) above, comprising applying the inhibitor for tobacco axillary bud growth described in any one of (1) to (3) above as a treatment solution containing 0.001 to 0.01 mass % of chlorthal-dimethyl and 0.5 to 2.5 mass % of aliphatic alcohol.

Effects of the Invention

The inhibitor for tobacco axillary bud growth of the present invention has a high effect of inhibiting axillary bud growth in a small amount and shows sustained chemical efficacy. Further, the inhibitor has no harmful effects on the stem and leaf parts and the root part. Therefore, in cultivation of tobacco, the inhibitor can achieve an increase in yield, improvement of quality, and improvement of labor productivity by reduction in labor for removing axillary buds.

MODE FOR CARRYING OUT THE INVENTION

The inhibitor for tobacco axillary bud growth of the present invention uses aliphatic alcohol selected from decyl alcohol, 2-ethyl hexanol and geraniol as well as chlorthal-dimethyl as an active ingredient.

The ratio of chlorthal-dimethyl and aliphatic alcohol used in the present invention is not particularly limited, and can be selected from a wide range depending on the combination of chlorthal-dimethyl and aliphatic alcohol to be selected.

It should be noted that the inhibitor for tobacco axillary bud growth of the present invention comprising chlorthal-dimethyl and aliphatic alcohol as an active ingredient encompasses an embodiment of an inhibitor formed by separately formulating the both components and appropriately mixing them before use.

The mixing ratio of the aliphatic alcohol to chlorthal-dimethyl is generally 1:2,500 to 1:50, preferably 1:700 to 1:70 in terms of mass ratio.

In the case of treating tobacco with the inhibitor for tobacco axillary bud growth of the present invention, it is recommended that the active ingredient concentration of chlorthal-dimethyl be 0.001 to 0.1 mass % and the active ingredient concentration of aliphatic alcohol be 0.5 to 2.5 mass %.

Although the inhibitor for tobacco axillary bud growth of the present invention may be used without adding any components other than chlorthal-dimethyl and the above-mentioned specific aliphatic alcohol, the inhibitor is usually mixed with a solid carrier, a liquid carrier or a gas carrier, and as necessary, is further supplemented with a surfactant, an extender, a colorant, a binder, an antifreezing agent, an ultraviolet absorber, or the like, to be formulated into an oil solution, an emulsion, a solubilizer, a wettable powder, a suspension, a flowable agent, a powder, or the like before application.

The surfactant is not particularly limited, and examples thereof include a phenylphenolsulfonic acid-formaldehyde condensate, sodium dioctyl sulfosuccinate, a sodium alkyl-naphthalene sulfonate, a polyoxyethylene alkyl phenyl ether, a sodium naphthalenesulfonate condensate, a sodium polyoxyethylene alkyl phenyl ether sulfoacetate, a ammonium polyoxyethylene alkyl phenyl ether sulfate, an ethylene oxide-propylene oxide copolymer, and an alkenyl sulfonate.

The extender is not particularly limited, and examples thereof include: plant powders such as soybean powder, tobacco powder, wheat powder, and wood powder; clay minerals such as clay, bentonite, acid clay, and radiolite; talcs such as talc powder and agalmatolite powder; mineral powders such as diatomaceous earth and mica powder; and sodium bicarbonate, calcium carbonate, alumina, and activated carbon.

The colorant is not particularly limited, and examples thereof include: inorganic pigments such as iron oxide, titanium oxide, and Prussian blue; organic dyes such as an alizarin dye, an azo dye, and a metallophthalocyanine dye; and trace elements such as iron, manganese, boron, copper, cobalt, molybdenum, and zinc.

The binder is not particularly limited, and examples thereof include carboxymethylcellulose sodium salt, starch, sodium lignin sulfonate, dextrin and polyvinyl alcohol.

The antifreezing agent is not particularly limited, and examples thereof include glycerin, ethylene glycol, and propylene glycol.

The ultraviolet absorber is not particularly limited, and examples thereof include substituted benzophenone, a diphenylacrylonitrile ester and a cinnamic acid ester.

As a tobacco (*Nicotiana tabacum*) cultivar which is suppressed by the inhibitor for tobacco axillary bud growth of the present invention in formation and elongation of axillary buds, there are given for example: domestic cultivars typified by Matsukawa, Daruma, Awa, and Siroenshu; flue-cured cultivars typified by Coker 319, Virginia 115, MC 1, Okinawa 2, Bright Yellow 4, Tsukuba 1, and Tsukuba 2; and burley cultivars typified by Burley 21, Kitakami 1, Michinoku 1 and Michinoku 2.

The use amount of the inhibitor for tobacco axillary bud growth of the present invention varies depending on the cultivar, method and timing of use, and the use amount of a spray solution per plant is desirably 5 to 40 ml, more desirably 15 to 30 ml.

In addition, with regard to the number of times of application of the inhibitor for tobacco axillary bud growth of the present invention, in the case where the first application is carried out before blooming of tobacco or before top pruning or in the case where tree vigor of tobacco is strong even after the first spraying after the top pruning, the inhibitor is effectively applied by performing the first application and subsequently the second spraying two weeks after the first application in the same manner as in the first application.

The inhibitor for tobacco auxiliary bud growth of the present invention may further contain known herbicides in order to enhance the efficacy. Examples of the herbicides include the following:

ioxynil, aclonifen, aziprotryne, acifluorfen-sodium, azimsulfuron, asulam, atrazine, azafenidin, amicarbazone, amidosulfuron, amitrole, aminocyclopyrachlor, aminopyralid, amiprophos-methyl, ametryne, alloxydim, isouron, isoxachlortole, isoxaflutole, isoxaben, isoproturon, imazaquin, imazapic, imazapyr, imazamethabenz-methyl, imazamoxammonium, imazethapyr, imazosulfuron, indaziflam, eglinazine-ethyl, esprocarb, ethalfluralin, ethametsulfuron-methyl, ethidimuron, ethoxysulfuron, ethoxyfen-ethyl, ethofumesate, etobenzanid, endothal disodium, oxadiazon, oxadiargyl, oxaziclomefone, oxasulfuron, oxyfluorfen, oryzalin, orthosulfamuron, orthobencarb, oleic acid, carfentrazone-ethyl, carbetamide, quizalofop-P-ethyl, quinoclamine, quinclorac, quinmerac, cumyluron, clethodim, clodinafop-propargyl, clopyralid, clomazone, chlomethoxyfen, clomeprop, cloransulam-methyl, chloramben, chlorimuron-ethyl, DCBN, chlorphthalim, chloroxuron, chlorsulfuron, chlornitrofen, chlorbufam, chlorflurenol-methyl, chlorpropham, chlorbromuron, chlorotoluron, chloroacetic acid, *Xanthomonas campestris*, cyanazine, sodium cyanate, cycloate, cycloxydim, diclosulam, cyclosulfamuron, dichlorprop, DBN, diclofop-methyl, diquat-dibromide, dithiopyr, siduron, dinitramine, cinidon-ethyl, cinosulfuron, dinoseb, dinoterb, cyhalofop-butyl, difenoxuron, difenzoquat, diflufenican, diflufenzopyr, dipropetryn, dimethametryn, simetryne, dimepiperate, dimefuron, simazine, cinmethylin, sulcotrione, sulfentrazone, sulfosulfuron, sulfometuron-methyl, sethoxydim, terbacil, terbuthylazine, terbutryne, dymron, dazomet, terbumeton, dalapon, thiazafluron, thiazopyr, thiencarbazone, tiocarbazil, thidiazimin, thifensulfuron-methyl, desmedipham, tetrapion, tebutam, tebuthiuron, tepraloxydim, tefuryltrione, desmetryne, tembotrione, topramezone, tralkoxydim, triaziflam, triasulfuron, tri-allate, trietazine, triclopyr, tritosulfuron, triofensulfuron, triflusulfuron-methyl, trifluralin, trifloxysulfuron-sodium, tribenuron-methyl, *Drechsrela monoceras*, naptalam, nicosulfuron, neburon, norflurazon, paraquat-dichloride, haloxyfop, halosafen, halosulfuron-methyl, bialaphos, picloram, picolinafen, bispyribac-sodium, pinoxaden, bifenox, pyrachlonil, pyrasulfotole, pyrazoxyfen, pyrazosulfuron-ethyl, pyrazolate, pyrazon, pyraflulfen-ethyl, pyridafol, pyrithiobac-sodium, pyridate, pyriftalid, pyributicarb, pyribenzoxim, pyrimisulfan, pyriminobac-methyl, pyroxasulfone, pyroxsulam, prometryne, fenuron, fenoxasulfone, fenoxaprop-P-ethyl, phenmedipham, fosamine-ammonium, fomesafen, foramsulfuron, butafenacil, butamiphos, butylate, butralin, butroxydim, flumetsulam, flazasulfuron, flamprop, primisulfuron-methyl, fluazifop, fluazolate, fluometuron, fluoroglycofen-ethyl, flucarbazone-sodium, fluchloralin, flucetosufuron, fluthiacet-methyl, flupyrsulfuron-methyl-sodium, flufenpyr-ethyl, flupoxam, flumioxazin, flumiclorac-pentyl, fluridone, flurenol, proglinazine-ethyl, prodiamine, prosulfuron, propaquizafop, propazine, propanil, propyzamide, propyrisulfuron, propham, profoxydim, profluazol, prosulfocarb, propoxycarbazone-sodium, bromacil, prometon, bromoxynil, bromofenoxim, bromobutide, florasulam, fluroxypyr, flurochloridone, flurtamone, hexazinone, benazolin-ethyl, benefin, penoxsulam, beflubutamid, pebulate, pelargonic acid, vernolate, bencarbazone), benzfendizone, bensulide, bensulfuron-methyl, benzobicyclon, benzofenap, bentazon, pentanochlor, benthiocarb, pendimethalin, pentoxazone, benfuresate, mesosulfuron-methyl, mesotrione, methasulfocarb, methabenzthiazuron, metamitron, metamifop, metazosulfuron, metam, MSMA (methylarsonic acid), methiozolin, methyldymron, metoxuron, metosulam, metsulfuron-methyl, methoprotryne, metobromuron, metobenzuron, metribuzin, monosulfuron, monolinuron, molinate, iodosulfuron-methyl-sodium, lactofen, linuron, rimsulfuron, lenacil, DCMU (Diuron), sodium chlorate, 2,3,6-TBA(2,3, 6-trichlorobenzoic acid), 2,4,5-T(2,4,5-trichlorophenoxyacetic acid), 2,4-DB(4-(2,4-dichlorophenoxy)butyric acid), 2,4-PA(2,4-Dichlorophenoxyacetic acid), DNOC(4,6-dinitro-O-cresol), EPTC(S-ethyl dipropylthiocarbamate), MCPA((4-chloro-2-methylphenoxy)acetic acid), MCPB(4-(4-chloro-2-methylphenoxy)butryric acid), MDBA (dicamba), sodium-trichloroacetate, hexanoic acid, heptanoic acid, octanoic acid, decanoic acid, undecanoic acid, dodecanoic acid, trimethyl hexanoic acid, cedar essence oil, cedarwood oil, Japanese cypress oil, eucalyptus oil, clove oil, citrus oil and lemon oil.

Further, the inhibitor for tobacco auxiliary bud growth of the present invention may further contain other insecticides, fungicides, plant growth regulators, fertilizers and the like to expand the range of action.

EXAMPLES

Examples of the present inventions are described hereinafter. Each example of formulations of chlorthal-dimethyl, decyl alcohol, 2-ethyl hexanol and geraniol is given first. The active ingredients, kinds of the additives and the compounding ratio thereof are not limited to the description set forth below and may be varied over a wide range. Here, the term "part(s)" means "part(s) by mass" and the term "%" means "mass %" in the following examples.

An emulsion containing 10% of chlorthal-dimethyl was obtained by dissolving 10 parts of chlorthal-dimethyl (manufactured by SDS BIOTECK K. K.) in 43 parts of N-methylpyrrolidone, adding thereto 22 parts of the mixture of 1-phenyl-1-xylyl ethane and 1-phenyl-1-ethylphenyl ethane (tradename: SAS 296; manufactured by Nippon Petrochemicals) and 25 parts of the mixture of polyoxyethylene styryl phenyl ether and alkyl aryl sulfonate (tradename: Sorpol 3880L; manufactured by TOHO CHEMICAL INDUSTRY Co., Ltd.) and stirring the mixture to be uniformly dissolved.

Formulation Example 1

An emulsion containing 70% of decyl alcohol was obtained by dissolving 10 parts of N-methylpyrrolidone, 10 parts of SAS 296 (tradename; manufactured by Nippon Petrochemicals) and 10 parts of Sorpol 3880L (tradename; manufactured by TOHO CHEMICAL INDUSTRY Co., Ltd.) in 70 parts of decyl alcohol (manufactured by Wako Pure Chemical Industries, Ltd.) and stirring the mixture to be uniformly dissolved.

Formulation Example 2

An emulsion containing 70% of 2-ethyl hexanol was obtained by dissolving 10 parts of N-methylpyrrolidone, 10 parts of SAS 296 (tradename; manufactured by Nippon Petrochemicals) and 10 parts of Sorpol 3880L (tradename; manufactured by TOHO CHEMICAL INDUSTRY Co., Ltd.) in 70 parts of 2-ethyl hexanol (manufactured by Wako Pure Chemical Industries, Ltd.) and stirring the mixture to be uniformly dissolved.

Formulation Example 3

An emulsion containing 70% of geraniol was obtained by dissolving 10 parts of N-methylpyrrolidone, 10 parts of SAS 296 (tradename; manufactured by Nippon Petrochemicals) and 10 parts of Sorpol 3880L (tradename; manufactured by TOHO CHEMICAL INDUSTRY Co., Ltd.) in 70 parts of geraniol (manufactured by Wako Pure Chemical Industries, Ltd.) and stirring the mixture to be uniformly dissolved.

Test Examples (Examples 1 to 18 and Comparative Examples 1 to 14)

Next, Test Examples are described below, which tests were conducted to confirm the efficacy of the inhibitor for tobacco auxiliary bud growth of the present invention. It should be noted that the mixing ratio of the active ingredients is not limited to those as described below and may be varied over a wide range.

Tobacco seedlings of Tsukuba 1 (flue-cured cultivar) were transplanted to 1/5000a Wagner pots filled with Kureha garden nursery soil. The plants were grown in a glasshouse, and the floral axis parts were removed at the time of single-flower bloom of tobacco (top pruning).

Samples were prepared by diluting the above-mentioned formulation containing 10% of chlorthal-dimethyl with water to predetermined concentrations, and adding thereto the formulation containing 70% of decyl alcohol so as to make each sample have a predetermined concentration, and subjected to the test (Examples 1 to 6). Samples were also prepared by diluting the formulation containing 10% of chlorthal-dimethyl with water to predetermined concentrations, and adding thereto the formulation containing 70% of 2-ethyl hexanol so as to make each sample have a predetermined concentration, and subjected to the test (Examples 7 to 12). Samples were also prepared by diluting the formulation containing 10% of chlorthal-dimethyl with water to predetermined concentrations, and adding thereto the formulation containing 70% of geraniol so as to make each sample have a predetermined concentration, and subjected to the test (Examples 13 to 18). Furthermore, as Comparative Examples, samples were prepared by diluting samples were also prepared by diluting the formulation containing 10% of chlorthal-dimethyl with water to predetermined concentrations (Comparative Examples 1 to 4), by diluting the formulation containing 70% of decyl alcohol with water to predetermined concentrations (Comparative Examples 5 to 7), and by diluting the formulation containing 70% of geraniol with water to predetermined concentrations (Comparative Examples 8 to 10), and by diluting the formulation containing 70% of geraniol with water to predetermined concentrations (Comparative Examples 11 to 13) to be subjected to the test. In addition, butralin (tradename: Blue Ribbon) (Comparative Example 14) was subjected to the test.

With respect to each of the formulations of the inhibitors for tobacco axillary bud growth, 20 ml of the water-diluted solutions of the respective inhibitors were separately sprayed using a contact-type axillary bud inhibitor spraying instrument equipped with a spot exhaust nozzle. One tobacco plant was planted per pot, and the tests were carried out in duplicate.

For the respective cases, states of inhibition of axillary bud growth 28 days after the spraying were investigated together with untreated groups sprayed with no inhibitor, and axillary bud growth inhibition rates were calculated by the following equation.

Axillary bud growth inhibition rate=(fresh weight of axillary buds per plant of untreated group−fresh weight of axillary buds per plant of treated group)÷(fresh weight of axillary buds per plant of untreated group)×100 [Math. 1]

Further, the presence or absence of the harmful effect of each inhibitor was evaluated in one of the following four categories depending on the degrees of growth inhibition, gangrene, change in color, deformation and the like of leaves (first to fourth leaves from the top).

Large: A severely harmful effect was observed.
Middle: A clearly harmful effect was observed.
Small: A slightly harmful effect was observed.
Absent: No harmful effect was observed.

For each of the examples, the axillary bud growth inhibition rate and the presence or absence of the harmful effects of the inhibitor are shown in Table 1.

TABLE 1

| | Compound(s) subjected to the test | Active ingredient concentration (%) | Axillary bud growth inhibition (%) | Harmful effect |
|---|---|---|---|---|
| Example 1 | Chlorthal-dimethyl + decyl alcohol | 0.002 + 0.7 | 63.6 (42.0) | None |
| Example 2 | Chlorthal-dimethyl + decyl alcohol | 0.002 + 1.4 | 100 (68.9) | None |

TABLE 1-continued

| | Compound(s) subjected to the test | Active ingredient concentration (%) | Axillary bud growth inhibition (%) | Harmful effect |
|---|---|---|---|---|
| Example 3 | Chlorthal-dimethyl + decyl alcohol | 0.005 + 0.7 | 82.1 (43.9) | None |
| Example 4 | Chlorthal-dimethyl + decyl alcohol | 0.005 + 1.4 | 100 (69.9) | None |
| Example 5 | Chlorthal-dimethyl + decyl alcohol | 0.01 + 0.7 | 92.5 (55.1) | None |
| Example 6 | Chlorthal-dimethyl + decyl alcohol | 0.01 + 1.4 | 100 (75.9) | None |
| Example 7 | Chlorthal-dimethyl + 2-ethyl hexanol | 0.002 + 0.7 | 54.9 (33.8) | None |
| Example 8 | Chlorthal-dimethyl + 2-ethyl hexanol | 0.002 + 1.4 | 100 (67.0) | None |
| Example 9 | Chlorthal-dimethyl + 2-ethyl hexanol | 0.005 + 0.7 | 78.4 (35.9) | None |
| Example 10 | Chlorthal-dimethyl + 2-ethyl hexanol | 0.005 + 1.4 | 100 (68.0) | None |
| Example 11 | Chlorthal-dimethyl + 2-ethyl hexanol | 0.01 + 0.7 | 87.5 (48.8) | None |
| Example 12 | Chlorthal-dimethyl + 2-ethyl hexanol | 0.01 + 1.4 | 100 (74.4) | None |
| Example 13 | Chlorthal-dimethyl + geraniol | 0.002 + 0.7 | 70.5 (52.6) | None |
| Example 14 | Chlorthal-dimethyl + geraniol | 0.002 + 1.4 | 100 (72.8) | None |
| Example 15 | Chlorthal-dimethyl + geraniol | 0.005 + 0.7 | 77.5 (54.1) | None |
| Example 16 | Chlorthal-dimethyl + geraniol | 0.005 + 1.4 | 100 (73.7) | None |
| Example 17 | Chlorthal-dimethyl + geraniol | 0.01 + 0.7 | 88.3 (63.3) | None |
| Example 18 | Chlorthal-dimethyl + geraniol | 0.01 + 1.4 | 100 (78.9) | None |
| Comparative Ex. 1 | Chlorthal-dimethyl | 0.002 | 1.1 | None |
| Comparative Ex. 2 | Chlorthal-dimethyl | 0.005 | 4.2 | None |
| Comparative Ex. 3 | Chlorthal-dimethyl | 0.01 | 23.4 | None |
| Comparative Ex. 4 | Chlorthal-dimethyl | 1 | 100 | None |
| Comparative Ex. 5 | Decyl alcohol | 0.7 | 41.4 | None |
| Comparative Ex. 6 | Decyl alcohol | 1.4 | 68.6 | None |
| Comparative Ex. 7 | Decyl alcohol | 2.6 | 86.8 | Small degree |
| Comparative Ex. 8 | 2-ethyl hexanol | 0.7 | 33.1 | None |
| Comparative Ex. 9 | 2-ethyl hexanol | 1.4 | 66.6 | None |
| Comparative Ex. 10 | 2-ethyl hexanol | 2.6 | 82.1 | Small degree |
| Comparative Ex. 11 | Geraniol | 0.7 | 52.1 | None |
| Comparative Ex. 12 | Geraniol | 1.4 | 72.5 | None |
| Comparative Ex. 13 | Geraniol | 2.6 | 87.9 | Medium degree |
| Comparative Ex. 14 | Butralin | 0.35 | 98.2 | Small degree |

It should be noted that the values in parentheses in Table 1 represent predicted values of the effects of inhibiting axillary bud growth of mixed agents (that is, compounds mixed as active ingredients), that is, expected values of additive effects. The expected values were calculated by the following Colby's equation (Colby. S. R.; "Calculating Synergistic and Antagonistic Responses of Herbicide Combinations" Weed, Vol. 15(1), 20-22, 1967).

Colby's equation: $E = x + y - x \cdot y/100$ [Math. 2]

E: Axillary bud growth inhibition rate in the case of using a mixture of active compound A (concentration a) and active compound B (concentration b) (theoretical axillary bud growth inhibition rate)

x: Axillary bud growth inhibition rate in the case of using active compound A at concentration a y: Axillary bud growth inhibition rate in the case of using active compound B at concentration b In the case where a measured value determined in the above-mentioned test (axillary bud growth inhibition rate) was larger than the expected value, a synergetic effect was expressed on activity to suppress axillary bud growth.

As shown in Table 1, all the measured values of the inhibitors for tobacco axillary bud growth of the present invention (Examples 1 to 18) are larger than the expected values due to the additive effects determined from the measured values of the agents including a single component (Comparative Examples 1 to 13), which shows that the inhibitors have synergistic effects. In order to obtain an effect of inhibiting axillary bud growth as high as that of the control agent (Comparative Example 14), chlorthal-dimethyl at a concentration of 1% (Comparative Example 4) is needed in the case of treating tobacco with the inhibitor comprising chlorthal-dimethyl as a single active ingredient. In contrast, in the case of treating tobacco with the inhibitor prepared by mixing chlorthal-dimethyl and either of decyl alcohol, 2-ethyl hexanol or geraniol, the concentration of chlorthal-dimethyl in the treatment liquid can be reduced to as low as 0.002% (Examples 2, 8 and 14). That is, the chlorthal-dimethyl concentration in the inhibitors for tobacco axillary bud growth of the present invention can be lowered to one five-hundredth of that in the case of treating tobacco with an inhibitor comprising chlorthal-dimethyl as a single active ingredient. Furthermore, while a small or medium degree of harmful effect was observed in the case of treating tobacco with an inhibitor comprising decyl alcohol, 2-ethyl hexanol or geraniol as a single active ingredient (Comparative Examples 7, 10 and 13) at a concentration of obtaining 80% of axillary bud growth inhibition rate, all the inhibitors for tobacco axillary bud growth of the present invention exhibited no harmful effect (Examples 1 to 18).

As apparent from the above, the inhibitor for tobacco axillary bud growth of the present invention has high effects of inhibiting axillary bud growth in a small amount as compared to existing inhibitors for tobacco axillary bud growth. In addition, it has been proved that the inhibitor for tobacco axillary bud growth of the present invention is superior also from the standpoint of causing no harmful effect.

The invention claimed is:

1. An inhibitor for tobacco axillary bud growth, comprising chlorthal-dimethyl and an aliphatic alcohol selected from the group consisting of decyl alcohol, 2-ethyl hexanol and geraniol, wherein said inhibitor is in the form of a treatment solution containing 0.001 to 0.01 mass % of chlorthal-dimethyl and 0.5 to 2.5 mass % of the aliphatic alcohol.

2. The inhibitor for tobacco axillary bud growth as claimed in claim 1, wherein the ratio of chlorthal-dimethyl and the aliphatic alcohol by mass is 1:2,500 to 1:50.

3. A method for inhibiting tobacco axillary bud growth, comprising applying the inhibitor for tobacco axillary bud growth as claimed in claim 1 to a tobacco plant.

4. The method for inhibiting tobacco axillary bud growth as claimed in claim 3, comprising applying the inhibitor for tobacco axillary bud growth as a treatment solution containing 0.001 to 0.01 mass % of chlorthal-dimethyl and 0.5 to 2.5 mass % of aliphatic alcohol.

* * * * *